United States Patent [19]

Barker et al.

[11] 4,070,363

[45] Jan. 24, 1978

[54] MANUFACTURE OF TETRAMISOLE

[75] Inventors: Alan Charles Barker; Peter Fulton Southern, both of Macclesfield, England

[73] Assignee: Imperial Chemical Industries Limited, London, England

[21] Appl. No.: 601,016

[22] Filed: Aug. 1, 1975

[30] Foreign Application Priority Data

Aug. 13, 1974 United Kingdom ............... 35594/74

[51] Int. Cl.$^2$ ........................................... C07D 513/04
[52] U.S. Cl. ............................................. 260/306.7 T
[58] Field of Search .................. 260/306.7 R, 306.7 T

[56] References Cited

U.S. PATENT DOCUMENTS

| | | | |
|---|---|---|---|
| 3,478,047 | 11/1969 | Doyle et al. ................. | 260/306.7 T |
| 3,642,809 | 2/1972 | Bullock ......................... | 260/306.7 T |
| 3,804,847 | 4/1974 | Blakeney et al. ............. | 260/306.7 T |

FOREIGN PATENT DOCUMENTS

| | | | |
|---|---|---|---|
| 1,304,088 | 1/1973 | United Kingdom .......... | 260/306.7 T |

OTHER PUBLICATIONS

Morrison et al. "Organic Chemistry," pp. 529–530 (1966).
Wagner et al., "Synthetic Organic Chemistry" N.Y., Wiley and Sons, 1953 pp. 89–91.
Guyot et al. "Chemical Abstracts" 1920, vol. 14 p. 1658.
Theilheimer, "Synthetic Methods", 1968, p. 273, set 590.

*Primary Examiner*—Raymond V. Rush
*Assistant Examiner*—David E. Wheeler
*Attorney, Agent, or Firm*—Cushman, Darby & Cushman

[57] ABSTRACT

Process for the manufacture of 2-imino-3-(2-chloro-2-phenylethyl)thiazolidine (known intermediate in manufacture of the anthelmintic agent tetramisole) by reacting 2-imino-3-(2-hydroxy-2-phenylethyl)thiazolidine with chlorosulphonic acid and either aqueous hydrochloric acid or water. Preferred procedure involves use of chlorosulphonic acid and concentrated hydrochloric acid.

10 Claims, No Drawings

MANUFACTURE OF TETRAMISOLE

Tetramisole (i.e. dl-2,3,5,6-tetrahydro-6-phenylimidazo[2,1-b]thiazole) and its pharmaceutically-acceptable acid-addition salts are known to be useful as anthelmintic agents. Furthermore, tetramisole is known to be useful for the manufacture, by resolution, of its laevo-isomer, levamisole, which is likewise useful as an anthelmintic agent. This invention relates to a new process for the manufacture of an intermediate used in the manufacture of tetramisole, and to a new process for the manufacture of tetramisole.

According to the invention there is provided a process for the manufacture of 2-imino-3-(2-chloro-2-phenylethyl)thiazolidine (hereinafter "ICPT") and acid-addition salts thereof, which comprises reacting 2-imino-3-(2-hydroxy-2-phenylethyl)thiazolidine (hereinafter "IHPT"), or an acid-addition salt thereof, with chlorosulphonic acid and either aqueous hydrochloric acid or water.

Suitable salts of IHPT for use as starting material are, for example, the p-toluenesulphonate and the hydrochloride. The chlorosulphonic acid may optionally be generated in situ in the reaction mixture from sulphuryl chloride in the presence of water (the chlorosulphonic acid itself reacting very quickly with the water to give sulphuric acid and hydrogen chloride). The aqueous hydrochloric acid may be, for example, concentrated hydrochloric acid, i.e., 12N-hydrochloric acid (36% w/w), and as pointed out below the use of concentrated hydrochloric acid is a preferred embodiment of this invention.

The yield of ICPT or acid-addition salt thereof obtained according to the above-mentioned process has been found to depend upon:

1. In cases where an acid-addition salt of IHPT is used as starting material, the specific salt which is used. It is to be understood that, in the case where IHPT is initially added as the free base, under the conditions of the reaction this is rapidly converted into a mixture of inter alia the hydrochloride and sulphate.

2. The amount of IHPT (or acid-addition salt thereof) relative to water in the reaction mixture.

3. The amount of the added chlorosulphonic acid relative to the water in the reaction mixture.

4. The amount of hydrochloric acid relative to water in the reaction mixture.

It is to be understood that some of the free water originally present in the reaction mixture is, in effect, withdrawn from the reaction mixture during the course of the process by solvation of protons in the reaction mixture. However, the references to water in points 1 to 4 above include free water and solvated water in the reaction mixture.

Reactions which are believed to be involved in the above-mentioned process of the invention are as follows:

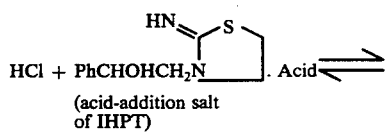

(acid-addition salt of IHPT)

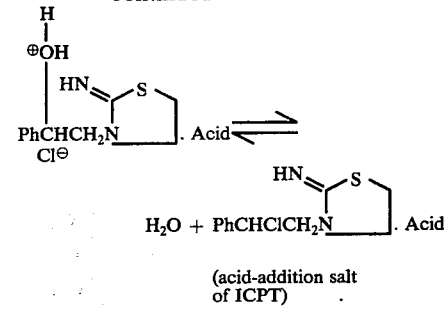

(acid-addition salt of ICPT)

High yields of the end-product are obtained when the above equilibrium is almost completely over to the right. The position of the equilibrium is governed by the concentration of HCl in free water. Guide-lines for the main types of situation which can arise in the present invention are as follows:

a. When a relatively low concentration of IHPT hydrochloride in water is used (such that the ratio of HCl:water is little changed from start to finish of the process) at least approximately 1/7 mol. of chlorosulphonic acid per mol. of water is needed. 1/6 mol. of chlorosulphonic acid per mol. of water is about optimum when 1/20 mol. of IHPT hydrochloride in water is used.

b. When a relatively low concentration of IHPT hydrochloride in concentrated hydrochloric acid is used, the use of any chlorosulphonic acid will give an improved yield of end-product. However, 1/16 mol. of chlorosulphonic acid per mol. of the water contained in the concentrated hydrochloric acid is about optimum when 1/12 mol. of IHPT hydrochloride in concentrated acid is used.

c. Using higher concentrations of IHPT hydrochloride, more chlorosulphonic acid is needed in cases (a) and (b) to keep the final HCl:water ratio satisfactory. The extra chlorosulphonic acid will not exceed approximately 1 mol. chlorosulphonic acid per mol. of IHPT hydrochloride.

d. When an acid-addition salt of IHPT other than the hydrochloride is used, more chlorosulphonic acid is needed in cases (a), (b) and (c) to keep the final HCl:water ratio satisfactory. The extra chlorosulphonic acid will not exceed approximately 1 mol. chlorosulphonic acid per mol. of IHPT salt.

The above-mentioned process of the invention may optionally be carried out at a moderately elevated temperature, for example at 30°-60° C., and more particularly at 45°-55° C.

At the beginning of the process of the invention hydrogen chloride gas is rapidly produced due to the interaction of chlorosulphonic acid with water. As this hydrogen chloride is an important reactant, the process is preferably carried out in a suitably closed plant or apparatus which prevents the loss of all of, or a substantial amount of, this hydrogen chloride. The process of the invention can be carried out at atmospheric pressure or (and this is preferred) at a moderately elevated pressure, the latter pressure being due to the hydrogen chloride gas which is generated from the reaction of chlorosulphonic acid (or sulphuryl chloride) and water.

A preferred embodiment of the invention comprises reacting IHPT, or an acid-addition salt thereof, and in particular the hydrochloride, with chlorosulphonic acid and concentrated hydrochloric acid.

This embodiment is preferred because less chlorosulphonic acid is required, and less total acid is required, both of which give processing advantages. In a particularly preferred embodiment, when the initial vigorous generation of hydrogen chloride gas has ended, the reaction mixture is heated at 45° to 55° C. for 6 to 10 hours, for example 8 hours.

It is known to manufacture ICPT and acid-addition salts thereof by reacting IHPT or an acid-addition salt thereof with a chlorinating agent, for example thionyl chloride or phosphorus oxychloride, but this process has the disadvantage that the product is contaminated with approximately 5% w/w of an unwanted impurity which is trans-2-imino-3-styrylthiazolidin (hereinafter "IST"). Special steps must be taken to remove this impurity from the ICPT or from tetramisole obtained from the latter, or alternative steps must be taken to reduce the amount of IST formed (see U.K. patent specification No. 1,304,088). The process of this invention has the advantage that no IST is produced as a by-product. The process also has the important practical advantage that a water-wet IHPT acid-addition salt can be used as starting material. That is, there is no necessity to dry the said salt (which is obtainable in a known manner) before using it in the process of the invention. Furthermore, the said salt in dry form has on occasions been found to be irritant to the skin and/or dermatitic, and the process of the invention avoids these problems.

The ICPT or ICPT acid-addition salt obtained according to the above-mentioned process may, without being isolated or purified, be ring-closed in a generally known manner by a process which involves the removal of the elements of HCl, for example by reaction with a basic inorganic substance, for example sodium hydroxide, so as to give tetramisole, and the latter may either be isolated as the free base or converted in known manner into an acid-addition salt thereof and isolated in that form.

According to a further feature of the invention, therefore, there is provided a process for the manufacture of tetramisole and acid-addition salts thereof, which comprises reacting IHPT, or an acid-addition salt thereof, with chlorosulphonic acid and either aqueous hydrochloric acid or water, and then in a generally known manner ring-closing the ICPT acid-addition salt thereby obtained so as to obtain tetramisole or an acid-addition salt thereof.

In a preferred embodiment, the first part of the last-named process is carried out according to the preferred embodiment described above.

The invention is illustrated but not limited by the following Examples:

EXAMPLE 1

IHPT p-toluenesulphonate (112.5 g., containing ca. 4 g. of impurities and ca. 22.5 g. of water) was added at room temperature to stirred concentrated hydrochloric acid (70 ml. of 12 N) in a reaction vessel. Chlorosulphonic acid (27 ml.) was added over 20 minutes from a pressure-equalising dropping funnel. The dropping funnel and the reaction vessel together formed a sealed system. At the end of the addition the mixture was heated at 50°–55° C. for 8 hours.

The reaction mixture, which contained ICPT in salt form, was poured into a mixture of ice (250 g.), caustic soda (115 ml. of 17.6 N), toluene (88 ml.) and butanol (22 ml.). This mixture was stirred and kept at 55° C. by heating. Sufficient caustic soda (17.6 N) was periodically added to keep the pH of the mixture at 9. When the mixture had stayed at pH 9 for 2 minutes without any caustic soda being needed (ca. 90 minutes after the beginning of the ring-closure process) the mixture was separated, both the aqueous and organic phases being kept. The aqueous phase was extracted with a mixture of toluene (88 ml.) and n-butanol (22 ml.). The organic extract was combined with the said organic phase. Water (250 ml.) was added to the stirred organic solution, and hydrochloric acid (ca. 20 ml. of 12 N) was added until the pH of the aqueous phase was 4. The two phases were separated, decolourising carbon (4 g.) and Celite (4 g.) were added to the aqueous phase, and the mixture was heated at 40°–45° C. for 30 minutes. The mixture was filtered, and the filtrate was adjusted to pH 9 with caustic soda (17.6 N) and then extracted twice with toluene (150 ml. and 100 ml.). Hydrochloric acid (12 N) was added slowly to the stirred combined toluene extracts, whereupon tetramisole hydrochloride precipitated. At intervals, a drop (ca. 0.1 ml.) of the toluene solution was spotted on to pH indicator paper, and a drop of water was dropped on the same spot, thus giving an indication of the amount of hydrogen chloride in the toluene. When the indicator paper gave a reading of pH 6, all of the precipitated tetramisole hydrochloride was filtered off, and as much water as possible was removed by suction. The solid was then washed with acetone (2 × 60 ml.) and dried in air at 50° C. There was thus obtained tetramisole hydrochloride of m.p. 255°–8° C.

EXAMPLE 2

IHPT hydrochloride (52.6 g.) was added to a mixture of concentrated hydrochloric acid (65 ml. of 12 N) and water (39 ml.) in a reaction vessel. Chlorosulphonic acid (32 ml.) was added slowly from a pressure equalising dropping funnel. The dropping funnel and the reaction vessel together formed a sealed system. At the end of the addition, the reaction mixture was stirred and heated at 48°–50° C. for 8 hours.

The reaction mixture, which contained ICPT in salt form, was poured into a mixture of ice (350 g.), sodium hydroxide solution (120 ml. of 17.6 N), toluene (88 ml.) and n-butanol (22 ml.). The temperature of this mixture was maintained at 50°–55° C. by heating and at pH 9.2–9.4 by dropwise addition of sodium hydroxide solution (17.6 N). When the pH had remained steady for 2 minutes without further addition of sodium hydroxide solution, the mixture was separated, both the aqueous and organic phases being kept. The aqueous phase was extracted with a mixture of toluene (81 ml.) and n-butanol (19 ml.). The organic extract was combined with the said organic phase, and stirred together with water (250 ml.). Concentrated hydrochloric acid (ca. 16 ml. of 12 N) was added until the pH of the aqueous layer was 4. The mixture was separated and the aqueous phase stirred with toluene (150 ml.). Sodium hydroxide solution (17.6 N) was added until the pH of the aqueous layer was 9. The mixture was separated (both the aqueous and organic phases being kept) and the aqueous phase was extracted with toluene (100 ml.). The organic extract was combined with the said organic phase, and tetramisole hydrochloride was isolated in the same manner as described in Example 1. It had m.p. 259°–60° C.

EXAMPLE 3

Concentrated hydrochloric acid (24.5 ml. of 12 N) and water (74 ml.) were added to IHPT p-toluenesulphonate (80 g.; containing ca. 5.6 g. of impurities) in a reaction vessel. This mixture was stirred and sulphuryl chloride (38 ml.) was added slowly from a pressure equalising dropping funnel, the temperature being maintained below 50° C. with cooling. The dropping funnel and reaction vessel together formed a sealed system. The reaction mixture was stirred and heated at 50°-55° C. for 8 hours.

The reaction mixture, which contained ICPT in salt form, was poured into a mixture of ice (350 g.), sodium hydroxide solution (120 ml. of 17.6 N), toluene (80 ml.) and n-butanol (30 ml.). The temperature of this reaction mixture was maintained at 50°-55° C. by heating and at pH 9.2-9.4 by dropwise addition of sodium hydroxide solution (17.6 N). When the pH had remained steady for 2 minutes without further addition of sodium hydroxide solution, the mixture was separated, both the aqueous and organic phases being kept. The aqueous phase was extracted with a mixture of toluene (73 ml.) and n-butanol (27 ml.), and the organic extract was combined with the said organic phase. The procedure used in Example 2 was then followed to give tetramisole hydrochloride of m.p. 258°-60° C.

EXAMPLES 4-14

(EXAMPLE 4)

IHPT hydrochloride (52.5 g.) was added at room temperature to 36% w/w hydrochloric acid (50 ml.) in a reaction vessel. Chlorosulphonic acid (10 ml.) was added over 4 minutes from a pressure equilising dropping funnel. The funnel and the reaction vessel together formed a sealed system. At the end of the addition the mixture was heated at 50° C. for 8 hours.

The reaction mixture, which then contained ICPT in salt form, was poured into a mixture of ice (115 g.), caustic soda (75 ml. of 17.6 N), toluene (80 ml.) and n-butanol (30 ml.). This mixture was stirred and kept at 55° C., by heating, for 2 hours. The mixture was then separated, both the organic and aqueous phases being retained, and the aqueous phase was extracted with a mixture of toluene (80 ml.) and n-butanol (30 ml.). The organic extract was combined with the said organic phase. Water (250 ml.) was added to the stirred organic solution, and 36% w/w hydrochloric acid was added until the pH of the aqueous phase was 4. The mixture was separated, and the aqueous phase was stirred with toluene (150 ml.). Sodium hydroxide solution (17.6 N) was added until the pH of the aqueous phase was 9. The mixture was separated, and the aqueous phase was extracted with toluene (100 ml.). Both organic extracts were combined. 36% w/w Hydrochloric acid was added to the stirred toluene solution, whereupon tetramisole hydrochloride precipitated. At intervals, a drop (ca. 0.1 ml.) of the toluene solution was spotted on to a pH indicator paper, and a drop of water was dropped on the same spot, thus giving an indication of the amount of hydrogen chloride in the toluene. When the indicator paper gave a reading of pH 6, all of the precipitated tetramisole hydrochloride was filtered off, and as much water as possible was removed by suction. The solid was then washed with acetone (2 × 60 ml.) and dried in the air at 50° C. There was thus obtained tetramisole hydrochloride of m.p. 260°-2° C. (yield 83%).

In a similar manner, but varying the amount of reactants etc. as indicated, tetramisole hydrochloride was obtained according to the following Examples 5-14. In each case the details are presented in the following order:

Example number; (1) amount of IHPT hydrochloride (and molar ratio thereof); (2) amount of chlorosulphonic acid (and molar ratio thereof); (3) amount of water (and molar ratio thereof); (4)(a) amount of 36% w/w hydrochloric acid, (b) molar ratio of water, and (c) molar ratio of HCl; (5) yield of tetramisole hydrochloride (%); (6) total water : chlorosulphonic acid, and (7)(a) amount of 17.6 N-sodium hydroxide and (b) amount of water (ml.) or ice (g.) used in the work-up procedure.

| Ex. | 1 | 2 | 3 | 4 | 5 | 6 | 7 |
|---|---|---|---|---|---|---|---|
| 5 | 52.5 g. (1) | 53 ml. (3.96) | 100 ml. (27.37) | — | 82.7 | 6.92 | (a) 140 ml. (b) 650 ml. |
| 6 | " | 40 ml. (2.98) | 70 ml. (19.16) | — | 82.1 | 6.42 | (a) 115 ml. (b) 500 ml. |
| 7 | " | 35 ml. (2.61) | " | — | 55.7 | 7.33 | (a) 100 ml. (b) 500 ml. |
| 8 | " | 15 ml. (1.12) | 13 ml. (3.56) | (a) 88 ml. (b) 18.06 (c) 5.13 | 82.1 | 19.3 | (a) 100 ml.* (b) 230 g. |
| 9 | " | 40 ml. (2.98) | 13.1 ml. (3.58) | (a) 40 ml. (b) 8.21 (c) 2.32 | 89.6 | 3.96 | (a) 135 ml. (b) 700 ml. |
| 10 | " | 10 ml. (0.75) | " | (a) 60 ml. (b) 12.32 (c) 3.48 | 61.3 | 21.25 | (a) 75 ml. (b) 420 ml. |
| 11 | " | 8 ml. (0.6) | — | (a) 50 ml. (b) 10.26 (c) 2.9 | 76.4 | 17.1 | (a) 70 ml. (b) 115 g. |
| 12 | " | 10 ml. (0.75) | — | (a) 60 ml. (b) 12.32 (c) 3.48 | 85.2 | 16.42 | (a) 80 ml. (b) 80 g. |
| 13 | " | " | — | (a) 80 ml. (b) 16.42 (c) 4.64 | 80.9 | 21.89 | (a) 86 ml. (b) 450 ml. |
| 14 | " | " | — | (a) 90 ml. (b) 18.47 (c) 5.25 | 76.8 | 24.67 | (a) 100 ml. (b) 150 g. |

*In Example 8 toluene (72 ml.) and n-butanol (28 ml.) were used, instead of the 80 ml. and 30 ml., respectively, of these solvents used in Examples 4 to 7 and 9 to 14.

EXAMPLES 15-19

The procedure described in Example 4 was repeated except that the duration of the reaction and the reaction temperature were varied as indicated. There was thus obtained tetramisole hydrochloride in the indicated yields:

| Example No. | Duration of reaction[1] (hours) | Temperature[2] (° C.) | Yield (%) |
|---|---|---|---|
| 15 | 90 | 30-34 | 75.4 |
| 16 | 38 | 40 | 83.1 |
| 17 | 8 | 60 | 86.1 |
| 18 | 6 | 60 | 72.9[3] |
| 19 | 4 | 60 | 66.8 |

1. This was the interval between the reaction temperature being reached and the cessation of heating.
2. This was the reaction temperature during the said interval.
3. Water (360 ml.) was used in place of the ice (115 g.) used in Example 4.

EXAMPLE 20

IHPT hydrochloride (127 g., containing ca. 23.5 g. of water and ca. 12.2 g. of impurities) was added at room temperature to stirred concentrated hydrochloric acid (176 ml. of 12 N) in a reaction vessel. Chlorosulphonic acid (30 ml.) was added over 7½ minutes from a pressure equilising dropping funnel. The dropping funnel and the reaction vessel together formed a sealed system. At the end of the addition the mixture was heated at 50° C. for 8 hours. The reaction mixture, which then contained ICPT in salt form, was poured into a mixture of ice (440 g.), caustic soda liquor (220 ml. of 17.6 N), toluene (144 ml.) and n-butanol (56 ml.). The mixture was stirred and maintained at ca. 55° C. during 2 hours. The mixture was separated, both aqueous and organic phases being kept. The aqueous phase was extracted with a mixture of toluene (144 ml.) and n-butanol (56 ml.). The organic extract was combined with said organic phase. Water (500 ml.) was added to the stirred organic solution, and hydrochloric acid (ca. 20 ml. of 12 N) was added until the pH of the aqueous phase was 4.5. The two phases were separated, decolourising carbon (3 g.) and Celite (2 g.) were added to the aqueous phase, and the mixture was heated at 40°-45° C. for 30 minutes. The mixture was filtered, and the filtrate was adjusted to pH 9 with caustic soda liquor (17.6 N) and then extracted twice with toluene (300 ml. and 200 ml.) tetramisole hydrochloride was isolated in the same manner as described in Example 1.

What we claim is:

1. In a process for the manufacture of ICPT and acid-addition salts thereof, which comprises reacting IHPT, or an acid-addition salt thereof, with hydrogen chloride gas as a chlorinating agent, the improvement which consists of generating the hydrogen chloride gas in situ by the reaction of chlorosulphonic acid with either aqueous hydrochloric acid or water.

2. The process claimed in claim 1 in which a water-wet IHPT acid-addition salt is used as starting material.

3. The process claimed in claim 1 wherein the chlorosulphonic acid is itself generated in the reaction mixture by the reaction of sulphuryl chloride with either aqueous hydrochloric acid or water.

4. The process claimed in claim 1 wherein the hydrogen chloride gas is generated by the reaction of chlorosulphonic acid with concentrated hydrochloric acid.

5. The process claimed in claim 4 wherein the hydrogen chloride gas so produced is reacted with IHPT hydrochloride.

6. The process claimed in claim 5 in which, when the initial vigorous generation of hydrogen chloride gas has ended, the reaction mixture is heated at 45° to 55° C. for 6 to 10 hours, whenever carried out in a plant or apparatus which is adapted to prevent the loss of all of, or a substantial amount of, the said hydrogen chloride gas.

7. In a process for the manufacture of tetramisole and acid-addition salts thereof which comprises reacting IHPT, or an acid-addition salt thereof, with hydrogen chloride gas as a chlorinating agent, to produce ICPT or an acid-addition salt thereof followed by reacting ICPT or an acid-addition salt thereof, with a basic inorganic substance to produce tetramisole which is either isolated as the free base or converted into an acid-addition salt thereof and isolated in that form, the improvement which consists of generating the hydrogen chloride gas in situ by the reaction of chlorosulphonic acid with either aqueous hydrochloric acid or water.

8. The process claimed in claim 7 wherein the hydrogen chloride gas is generated by the reaction of chlorosulphonic acid with concentrated hydrochloric acid.

9. The process claimed in claim 8 in which, during the reaction of IHPT, or an acid-addition salt thereof, with chlorosulphonic acid and concentrated hydrochloric acid, when the vigorous generation of hydrogen chloride gas has ended, the reaction mixture is heated at 45° to 55° C. for 6 to 10 hours.

10. A process as claimed in claim 7 wherein IHPT hydrochloride is reacted with chlorosulphonic acid and concentrated hydrochloric acid, and when the generation of the initially produced hydrogen chloride gas has ended the reaction mixture is heated at 45°-55° C. for 6 to 10 hours, whenever carried out in a plant or apparatus which is adapted to prevent the loss of all of, or a substantial amount of, the hydrogen chloride gas which is initially generated.

* * * * *